United States Patent [19]

Albertson

[11] Patent Number: 4,557,809

[45] Date of Patent: Dec. 10, 1985

[54] ELECTROCHEMICAL SYNTHESIS OF ZEROVALENT TRANSITION METAL ORGANOPHOSPHORUS COMPLEXES

[75] Inventor: Clarence E. Albertson, Villa Park, Ill.

[73] Assignee: Borg-Warner Chemicals, Inc., Parkersburg, W. Va.

[21] Appl. No.: 722,471

[22] Filed: Apr. 12, 1985

[51] Int. Cl.[4] .................................................. C25C 1/00
[52] U.S. Cl. ........................... 204/59 QM; 204/59 M; 204/DIG. 9
[58] Field of Search ......... 204/59 M, 59 QM, DIG. 9

[56] References Cited

U.S. PATENT DOCUMENTS

| | | | |
|---|---|---|---|
| 3,152,158 | 10/1964 | Clark | 260/439 |
| 3,328,443 | 6/1967 | Clark et al. | 260/439 |
| 3,346,608 | 10/1967 | von Kutepow et al. | 260/439 |
| 3,631,191 | 12/1971 | Kane et al. | 260/439 R |
| 3,668,086 | 6/1972 | Hughes | 204/59 R |
| 3,669,999 | 6/1972 | Levine | 260/439 R |
| 3,773,632 | 11/1973 | Lehmkuhl | 204/59 QM |
| 3,887,441 | 6/1975 | Hughes et al. | 204/59 QM |
| 3,903,120 | 9/1975 | Shook, Jr. et al. | 260/439 R |
| 4,012,399 | 3/1977 | Hechenbleikner et al. | 260/439 R |
| 4,222,898 | 9/1980 | Noltes et al. | 252/447 |

OTHER PUBLICATIONS

C.A. 78, 143297y (1973); C.A. 83, 100253s (1975); C.A. 81, 85367v (1974).

The Application of Pulsed Current Electrolysis to a Rotating-Disk Electrode System, K. Viswanathan, et al., J. Electrochem. Soc.: Electrochemical Science and Technology, vol. 125, No. 11 (1978), pp. 1772-1776.

Electrochemical Synthesis of Tris(Tri-o-tolylphosphite)nickel(O), B. Corain et al., Inorganica Chimica Acta, 26 (1978), pp. 37-40.

Fundamental Aspects of Pulsed Plating, H. Y. Cheh, International Pulse Plating Symposium, Apr. 19-20, 1979, Boston, Mass.

Primary Examiner—John F. Niebling
Attorney, Agent, or Firm—Emily A. Richeson

[57] ABSTRACT

An electrochemical process is provided for the production of a zerovalent metal/organo-phosphorus ligand complex by passing a current through an electrolyte bath which includes a transition metal salt and a trivalent organic phosphorous compound, the improvement comprising the current being a pulsed direct current.

12 Claims, No Drawings

ELECTROCHEMICAL SYNTHESIS OF ZEROVALENT TRANSITION METAL ORGANOPHOSPHORUS COMPLEXES

BACKGROUND OF THE INVENTION

The present invention relates generally to an improved electrochemical process for the production of complexes of a zerovalent transition metal and at least one trivalent organic phosphorus ligand.

Zerovalent organo-metal complexes have many known uses in the production of various chemical feedstocks and products. These applications include use as catalysts for a variety of reactions, such as the oligomerization of dienes, the isomerization of alkenes and dienes, the hydrogenation of unsaturated organic compounds, or the co-dimerization of olefins or alkynes with diolefins. These complexes may alternatively be subjected to thermal decomposition to provide a substrate with a metal coating.

A variety of chemical processes for producing zerovalent organo-metal complexes are known in the art. One such method is disclosed in U.S. Pat. No. 3,631,191 to Kane. This process involves contacting divalent nickel with a triaryl phosphite and a reducing metal under reaction conditions. However, many chemical processes have the disadvantage of requiring reducing agents, such as organo-metal complexes, which are relatively difficult to handle. It is in part for this reason that electrochemical processes for producing zerovalent organo-metal complexes have been developed.

Electrochemical processes for the synthesis of zerovalent organo-metal complexes are disclosed by U.S. Pat. No. 3,668,086 to Hughes, U.S. Pat. No. 3,887,441 to Hughes and Fahey and U.S. Pat. No. 3,773,632 to Lehmkuhl, as well as the article "Electrochemical Synthesis of Tris(Tri-o-tolylphosphite)nickel(0)", Corain, Bontempelli, De Nardo and Mazzocchin, Organica Chimica Acta 26 (1978) 37–40. Complexes produced by these methods include tris(tri-o-tolylphosphite)nickel(0), nickel tetra(triphenylphosphine), tris(cyclooctatetraene)dimanganese, tetra(tri-n-butylphosphine)nickel, trans-cyclodecatriene-(1,5,9)-nickel and cyclooctenyl-cobalt-cyclooctadiene-(1,5).

Although known electrochemical processes may be used to synthesize zerovalent organophosphorus transition metal complexes, these processes often result in the transition metal plating onto the cathode. This plating necessitates adding a transition metal recovery step to the process to minimize loss of the metal. More importantly, this plating tends to flake off of the cathode during the process and to circulate in the catholyte as finely divided particles of metal, which contributes to loss of the metal and makes isolation of a pure product relatively difficult, if not impossible. Although prior processes have sought to avoid the occurence of metal flakes in the catholyte by utilizing a large excess of the organic ligand, this may contribute significantly to the cost of the process.

It has been discovered, however, that plating of transition metal onto the cathode and the presence of metal particles in the catholyte may be minimized or avoid by the improvement of the present invention, so that a relatively pure organo-phosphorus/metal complex may be obtained. It has further been discovered that incorporation of the improvement of the present invention into an electrochemical process may result in increased product yields.

SUMMARY OF THE INVENTION

The present invention is an improvement in a process for producing a zerovalent metal/organo-phosphorus ligand complex by passing a current through an electrolyte bath which includes a transition metal salt and a trivalent organic phosphorus compound, wherein the improvement comprises the current being a pulsed direct current. Trivalent phosphorus compounds such as phosphites, phosphines, phosphinites and phosphonites are generally preferred. It is also preferred that the process utilize an inert cathode, and a metal powder anode which consists essentially of the same transition metal as the transition metal salt. Cathode current densities of about 5 to about 20 milliAmperes per square inch (mA/sq. in.) are preferred.

DETAILED DESCRIPTION OF THE INVENTION

The present invention is an improvement in an electrochemical process wherein a complex of a zerovalent metal and at least one organo-phosphorus ligand is produced by passing a current through an electrolyte bath that includes a transition metal salt and a trivalent organic phosphorus compound. The improvement comprises the current being a direct current which is pulsed.

As is known in the art, a variety of transition metals may be employed in electrochemical processes to produce zerovalent organo-metal complexes. These metals may include Co, Ni, Ru, Rh, Pd, Os, Ir and Pt, Group VB, VIB and VIIB metals, such as Ti, V, Cr, Mo, and Mn. Preferably, however, the transition metal is selected from the group consisting of Co, Ni, Ru, Rh, Pd, Os, Ir and Pt. Transition metals selected from the group consisting of Ni, Co, Pd and Pt are more preferred, with Ni being most preferred.

These transition metals are usually introduced to the bath in the form of a salt of the transition metal. A variety of suitable transition metal salts are known, such as chlorides, bromides, acetates, and acetonylacetones. Examples of such salts include cobalt bromide, cobalt chloride, nickel chloride, nickel acetate, nickel bromide, platinum chloride, platinum dibromide, platinum dichloride, rhodium trichloride, ruthinium trichloride, manganese acetylacetonate, chromium acetate and chromium acetylacetonate. Preferably, this salt should be one which is soluble in significant amounts in the electrolyte bath.

A variety of trivalent organic phosphorus compounds may be used to form complexes with zerovalent transition metals. Such trivalent organo-phosphorus compounds include phosphines, phosphinites, phosphonites or phosphites. These compounds may be generally described by the formula: $PRR'R''$, wherein each of R, R' and R'' independently is an alkyl, alkoxy, aryl or aryloxy moiety. Many such organo-phosphorus compounds are known in the art, such as trimethylol heptadecane phosphite, tris-octadecyl phosphite, tri(2-ethylhexyl)phosphite, tri-methylol undecane phosphite, tripentyl phosphine, tri(p-methoxyphenyl)phosphite, amyl dibutyl phosphite, tri(propylphenyl)phosphite and tri(ethylphenyl)phosphite.

One or more of R, R' and R'' may be an alkyl or aryl moiety, such as in phosphines, phosphinites and phosphonites, such as triethyl phosphine, dimethylphenyl phosphine, trimethyl phosphine, triphenyl phosphine, methyl diphenyl phosphinite, diphenyl ether phosphine and methyl diphenyl phosphonite. It is preferred, however, that R, R' and R" be independently selected from the group consisting of alkoxy and aryloxy moieties, so that the organo-phosphorus compound is a phosphite.

Although one or more of R, R' and R" may be a relatively large moiety of 15, 18 or more carbon atoms, R, R' and R" preferably are independently selected from the group consisting of alkoxy moieties having 1 to about 8 carbon atoms, and aryloxy moieties which have from 1 to about 10 carbon atoms. Examples of such moieties include methoxy, ethoxy, propoxy, phenoxy, t-butylphenoxy and methylphenoxy. Examples of trivalent organo-phosphorus compounds consistent with the preferred embodiment include triisopropyl phosphite, tri(p-methoxyphenyl)phosphite, triphenyl phosphite, trimethyl phosphite, amyl dibutyl phosphite, triethyl phosphite, tributyl phosphite, and tri-p-methylphenyl phosphite. Trivalent phosphorus compounds wherein R, R' and R" are the same moiety selected from the group consisting of $C_1$ to about $C_8$ alkoxy and $C_1$ to about $C_{10}$ aryloxy moieties are even more preferred, with trimethyl phosphite being most preferred.

In the alternative, less preferred embodiment wherein at least one of R, R' and R" is an alkyl or aryl moiety, it is preferred that R, R' and R" be selected from the group consisting of $C_1$ to about $C_8$ alkyl moieties and $C_1$ to about $C_{10}$ aryl moieties. Examples of moieties consistent with this embodiment include methyl, ethyl, propyl, butyl, pentyl, octyl, nonyl, phenyl, cyclohexyl, methylphenyl, ethylphenyl and methoxy phenyl.

According to the process of the invention, the electrolyte bath is a liquid capable of dissolving significant quantities of the transition metal salt and the trivalent organic phosphorus compound therein. This liquid preferably is an organic solvent which ionizes at least slightly when the current passes through the bath. Such solvents are known in the art, and include solvents such as acetonitrile, tetrahydrofurane, dimethoxyethane, pyridine, propionitrile, N,N-dimethylformamide, methanol, ethanol, sulfolane, methylene chloride and dioxane. Under most conditions, however, acetonitrile, tetrahydrofurane and N,N-dimethylformamide are preferred, with acetonitrile being most preferred. A conductive salt, such as tetrbutylammonium iodide, which is soluble in the ligand and the electrolyte bath may also be included to improve the conductivity of the bath. Other suitable conductive salts and their uses are known in the art.

The material used for the cathode and anode will depend, at least in part, on the identity of the transition metal. The cathode may be made of any material which is relatively chemically inert in the electrolyte bath under the process conditions, such as stainless steel, aluminum, mercury, lead, graphite and other materials known in the art. While the anode may be formed from a variety of materials, such as metal powder or a carbon rod, it is preferred that the anode be formed by the powder of the same transition metal as the transition metal salt in the electrolyte bath. For example, when the transition metal salt is a nickel salt, such as nickel chloride, it is preferred that the anode by a nickel powder anode; when the metal salt is a cobalt salt such as cobalt chloride, the anode preferably is a cobalt powder anode, and so forth.

It is critical to the present invention that the current which is passed through the bath be a pulsed or intermittent direct current, such as that provided by transmitting a half-wave rectified current through the bath. As is known in the art, the voltage most appropriate for a particular process will be dependent upon the geometry of the electrolytic cell, the conductivity of the bath and the bath temperature. This voltage is not critical to the process, with its adjustment being within the means of the skilled artisan. For most processes, however, voltages of between about 20 and about 100 volts will be preferred. Although the current density at the cathode is not critical to the invention, it is preferred that the cathode current density be about 5 milliamperes per square inch (mA/sq. in.) to about 20 mA/sq. in.

The molar ratio of the trivalent organo-phosphorus compound to the transition metal may be any amount equal to or greater than the ratio with which the phosphorus compound becomes complexed with the transition metal in the zerovalent state. I.e., to produce tetrakis complexes, the molar ratio of organo-phosphorus compound to metal should be at least 4:1; to produce hexakis complexes, such as hexakis (tripentyl phosphine)molybdenum, the ratio should be at least 6:1. As most of the transition metals of the preferred embodiment become coordinated with at least 4 phosphorus compounds in the zerovalent state, molar ratios of phosphorus compound to transition metal of at least 4:1 are preferred. The upper limit of this ratio is usually determined by solubility of the metal salt and the organo-phosphorus compound, by convenience, and by economics. However, in most applications the molar ratio of the organo-phosphorus compound to the transition metal will be less than 15:1. Molar ratios of organic phosphorus compound to transition metal wherein the phosphorus compound is not present in extremely large excess relative to the metal, such as about 10:1 to about 5:1, are most preferred.

The temperature at which the process of the present invention is conducted is not critical, but may be any temperature compatible with the salt, organic phosphorus compound and solvent selected and the product to be obtained. This temperature also should be below the boiling point of the solvent, product and reactants at the pressure under which the process is performed. Usually, however, temperatures of about 20° C. to about 100° C. are appropriate.

The process of the present invention is normally performed under anhydrous conditions and an inert atmosphere, such as that provided by nitrogen or argon, in order to remove any oxygen which may be present. The process is usually carried out in a cell of any appropriate dimension and configuration. This cell is normally provided with a porous partition, such as a porcelain diaphragm, between the cathode and anode to diminish diffusion of product to the anode and reoxidation of the transition metal. This process may be conducted as either a batch process, wherein the process continues for as long as desired or until the conductance drops, or as a continuous process, wherein bath solution is continuously removed and subjected to product separation methods, such as extraction, at the same time that fresh or recycled solution is added to the bath.

In addition to this description, the process of the present invention may be further understood by reference to the illustrative, nonlimiting examples provided below.

Comparative Example C1 exemplifies the preparation of a zerovalent transition metal/trivalent organo-phosphorus compound complex in a methanol bath, using continuous, rather than pulsed, direct current.

SPECIFIC EMBODIMENTS

COMPARATIVE EXAMPLE C1

A cell was set up with a porous ceramic cup diaphragm dividing the cell into a cathode chamber and an anode cup. A carbon rod anode was fitted with a rubber stopper and contacted with 50 g of nickel powder in the ceramic anode cup. A 15 sq. in. stainless steel wire screen cathode was positioned in the cathode chamber. The cathode compartment contained, in addition to the cathode lead, an inlet for inert gas and an outlet tube connected to a bubbler. About 115 mL of nickel chloride ($NiCl_2$) saturated methanol solution was poured into the cathode chamber and the cell purged with argon. Trimethylphosphite (TMP), 15 g, was syringed into the electrolyte in the cathode chamber. About 15 mL $NiCl_2$ saturated methanol was syringed into the anode cup to wet the nickel powder. The cell was operated for $4\frac{1}{2}$ hours at 0.2 to 0.06 amp., 3 V to 5 V, filtered, continuous direct current, at room temperature, with agitation. About every one half hour 15 mL of the anolyte solution was syringed into the catholyte, because the current carried the electrolyte into the anode compartment. Metallic flecks were observed circulating in the catholyte. These metallic flecks were nickel which plated onto the cathode and then spalled off into the solution. This indicated that a significant portion of the $NiCl_2$ was converted to metallic nickel instead of a zerovalent complex with TMP. At the end of this run the solution was a reddish brown, indicating the presence of the intermediate $NiCl_2 \cdot (TMP)_2$. After standing overnight the color of the solution had changed to green, the color of $NiCl_2$, thereby indicating $NiCl_2 \cdot (TMP)_2$ had been depleted, possibly by hydrolysis. For this reason the solutions in the subsequent examples were extracted promptly with hexane after the end of each run.

Example 2 exemplifies the preparation of a zerovalent metal/organo-phosphorus complex in a methanol bath, using a pulsed direct current according to the invention.

EXAMPLE 2

A cell was set up according to the configuration described for Comparative Example C1. Fresh electrolyte was made by agitating excess $NiCl_2$ in 200 mL methanol for 2 hours at 50° C. under argon. The electrolyte solution, 110 mL, and 16 g trimethylphosphite (TMP) were used to fill the cell under argon. The cell was operated for approximately $6\frac{3}{4}$ hours at room temperature using a pulsed direct current of about 0.2 amp. The electrolyte was transferred in 15 mL portions from the anode chamber to the cathode chamber at 15 minute intervals. About 1.32 amp. hours of current were used, the equivalent of 12.11 g TMP reacted out of 16 g charged. After the cell was shut down the electrolyte was immediately extracted with 100 mL of hexane, which is capable of solubilizing the tetra(trimethylphosphite)-zerovalent nickel complex, but is incapable of solubilizing significant quantities of the nickel salt or the $NiCl_2 \cdot (TMP)_2$ complex. Product yield recovered by one extraction was about 22% of the theoretically possible yield. The cathode had the same weight after the test as before the experiment was begun, and showed no evidence of nickel plating. No metal was observed circulating in the catholyte.

Example 3 exemplifies a process for preparing a zerovalent metal/organo-phosphorus complex in an acetonitrile bath, using a pulse direct current according to the present invention.

EXAMPLE 3

The electrolyte was made by stirring 225 mL of acetonitrile with excess $NiCl_2$ and 30 g trimethylphosphite for 1 hour at 50° C. under argon. This mixture was allowed to settle overnight, and the solids separated. A cell was set up and operated as described for Comparative Example 1, except that the solvent was acetonitrile and the current employed was a pulsed direct current at 0.15 amp. for a total of about 0.94 amp. hrs. current or the equivalent of about 8.6 g TMP complexed out of the approximately 15 g charged. The electrolyte was observed to migrate out of the cup, in a direction opposite to that of the methanol based electrolyte. Electrolyte was syringed from the cathode chamber into the anode chamber at about 45 minute intervals. A temperature of about 33° C. was observed in a water bath surrounding the cell. The cell was operated for slightly less than 8 hours, after which the electrolyte was extracted with hexane. The hexane was subsequently evaporated under vacuum to leave a white crystalline solid. Product yield was about 26% for single extraction recovery based upon the theoretically possible yield. No evidence was observed of nickel plating on the cathode screen, nor were any metallic flakes observed circulating in the catholyte.

The procedure described below in Comparative Example C4 was undertaken to evaluate whether significant quantities of zerovalent transition metal/organophosphorus complex form in a solution analogous to that described in Example 3, in the absence of either pulsed or continuous current.

COMPARATIVE EXAMPLE C4

Excess dehydrated nickel chloride was added to acetonitrile, stirred and warmed to 40° C. to form a saturated solution. After settling, 200 mL of the solution, 30 g TMP and 5 g of nickel powder were mixed under nitrogen and magnetically stirred at room temperature for 24 hours. During this process the solution changed to a color indicating the presence of $NiCl_2 \cdot (TMP)_2$. After standing overnight, the mixture was extracted with 100 mL hexane and separated. The hexane extract was vacuum distilled at temperatures below 20° C., leaving no visible residue. Thus it appears that formation of the zerovalent nickel complex of TMP does not occur to a significant extent in the absence of electric current.

Example 5 exemplifies preparation of a zerovalent transition nickel/trimethyl phosphite complex according to the process of the present invention.

EXAMPLE 5

A cell was set up as described in Comparative Example C1, above. A 1/16 in. hole was drilled in the bottom of the anode cup to allow electrolyte seepage to equalize catholyte and anolyte levels. Electrolyte was prepared using about 0.42 g $NiCl_2$, 16 g TMP and 200 cc acetonitrile. The cell was charged with 145 cc of electrolyte, containing about 10.5 g TMP. Tetrabutylammonium iodide, $\frac{1}{2}$ g, was added to the electrolyte. Two hours after current was initiated, the cell was heated to approximately 35° C. A pulsed, diode controlled direct current was used, for a total of 0.99 amp. hours of current, or 86% of that theoretically required for complete electrolysis. Approximately 1 g of a white crystalline product was recovered after extraction of the electrolyte with hexane and distillation of the hexane under vacuum. The presence of Ni(0)(TMP)$_4$ was confirmed by nuclear magnetic resonance analysis (NMR). No tetrabutylammonium iodide was detected in the product.

Example 6 exemplifies preparation of a zerovalent palladium/trimethyl phosphite complex in acetonitrile, using a pulsed direct current according to the process of the present invention.

EXAMPLE 6

A palladium chloride (PdCl$_2$) solution of 5 g PdCl$_2$, 14 g TMP and ½ g tetrabutylammonium iodide in 130 cc acetonitrile was made. The cell was set up according to that described above for Example 5. The cell was heated to 35° C. except that an active carbon anode was used to absorb Cl$_2$. A pulsed direct current was passed through the cell for approximately 6¾ hours for a total of 1.26 amp. hrs. of current used. About 0.34 g of a white crystalline product, or about 2.4% of the theoretical yield, was recovered by extraction of the electrolyte with hexane, followed by hexane distillation under vacuum. NMR analysis indicated the product to be tetra(-trimethylphosphite)palladium(0).

COMPARATIVE EXAMPLE C7

The procedure of Example 6 was repeated, except that the current was continuous. About 1.42 amp. hours of current was used. This resulted in 0.18 g of white crystalline product, confirmed by NMR analysis to be tetra(trimethylphosphite)palladium(0). Product yield was about 1.1% of the theoretical yield, or approximately only about ½ of the yield obtained when a pulsed current was used.

Example 8 exemplifies preparation of a zerovalent cobalt/trimethyl phosphite complex according to the process of the invention.

EXAMPLE 8

A cell was set up according to that described above for Example 5, using a cobalt powder anode. A solution of 2.2 g of cobalt chloride (CoCl$_2$) and 15 g TMP in 150 cc of acetonitrile was prepared and placed in the cell. A pulsed direct current was passed through the cell for approximately 6½ hours for a total of about 0.98 amp. hours. About 0.4 g, or about 4% of the theoretical yield, of a clear, white crystalline product was recovered. NMR analysis revealed the presence of tetrakis(trimethylphosphite)cobalt(0). This analysis also revealed a trace contamination of tetra(trimethylphosphite)nickel(0), possibly from the stainless steel cathode.

As is apparent from the above examples, the process of the present invention may be employed to minimize problems associated with plating onto the cathode and loss of metal, while providing zerovalent transition metal/organo-phosphorus complexes in a yield which may be higher than that realized from processes of the prior art. The present invention will thus be seen to be an improved electrochemical process for the production of a zerovalent metal/organo-phosphorus ligand complex by passing a current through an electrolyte bath that includes a transition metal salt and a trivalent organo-phosphorus compound, wherein the improvement comprises the current being a pulsed direct current.

It will be understood that various changes and modifications may be made in the embodiments described above without departing from the spirit of the invention, which includes all equivalents and modifications thereof and is limited only by the following claims.

I claim:

1. An electrochemical process for the production of a zerovalent metal/organo-phosphorus ligand complex by passing a current through an electrolyte bath which includes a transition metal salt and a trivalent organo-phosphorus compound, the improvement comprising said current being a pulsed direct current.

2. The process of claim 1 wherein the trivalent organo-phosphorus compound is described by the general formula: PRR'R", wherein R, R' and R" are independently selected from the group consisting of alkyl, alkoxy, aryl and aryloxy moieties.

3. The process of claim 2 wherein R, R' and R" are independently selected from the group consisting alkoxy and aryloxy moieties.

4. The process of claim 3 wherein R, R' and R" are independently selected from the group consisting of C$_1$ to about C$_8$ alkoxy and C$_1$ to about C$_{10}$ aryloxy moieties.

5. The process of claim 1 wherein said transition metal salt includes a transition metal selected from the group consisting of Co, Ni, Ru, Rh, Pd, Os, Ir, and Pt.

6. The process of claim 5 wherein said transition metal is selected from the group consisting of Ni, Co, Pd and Pt.

7. The process of claim 1 wherein said electrolyte bath includes an ionizing organic solvent and said transition metal salt and said trivalent organo-phosphorus compound are dissolved in the bath.

8. The process of claim 1 wherein the molar ratio of said organo-phosphorus compound to said transition metal is at least 4:1.

9. The process of claim 8 wherein the molar ratio of said phosphorus compound to said transition metal is less than 15:1.

10. The process of claim 9 wherein the molar ratio of said organo-phosphorous compound to said metal is about 10:1 to about 5:1.

11. The process of claim 1 wherein said bath has immersed therein an inert cathode, and a transition metal powder anode which consists essentially of the same transition metal included in the transition metal salt.

12. The process of claim 1 wherein said current has a cathode current density of about 5 to about 20 milliAmperes per square inch.

* * * * *